United States Patent [19]

Symon et al.

[11] 4,415,663

[45] Nov. 15, 1983

[54] SUPPORT MATRIX FOR IMMOBILIZED ENZYMES

[75] Inventors: Ted Symon, Lombard; Chester F. Barszcz, Chicago, both of Ill.

[73] Assignee: UOP Inc., Des Plaines, Ill.

[21] Appl. No.: 411,157

[22] Filed: Aug. 25, 1982

[51] Int. Cl.$^3$ .................... C12N 11/14; C12N 11/08; B01J 31/02; B32B 17/10
[52] U.S. Cl. ................... 435/176; 428/441; 428/451; 435/180; 502/150
[58] Field of Search ............... 428/411, 417, 418, 441, 428/451, 457, 458, 426; 252/430, 428; 435/174, 176, 180, 181

[56] References Cited

U.S. PATENT DOCUMENTS 4,141,857  2/1979  Levy .................... 252/430

FOREIGN PATENT DOCUMENTS 755296  8/1980  U.S.S.R. .................... 252/428

Primary Examiner—George F. Lesmes
Assistant Examiner—Beverly K. Johnson
Attorney, Agent, or Firm—James R. Hoatson, Jr.; Eugene I. Snyder; William H. Page, II

[57] ABSTRACT

A support matrix comprising a porous support impregnated with a polyamine substantially all of whose nitrogens bear pendant epoxide groups can be readily used to immobilize enzymes. Because immobilization results from formation of a hydrolytically stable carbon-nitrogen single bond, the resulting immobilized enzyme system may be advantageously used where hydrolytic instability of the bound enzyme is an important consideration.

15 Claims, No Drawings

SUPPORT MATRIX FOR IMMOBILIZED ENZYMES

BACKGROUND OF THE INVENTION

Because enzymes can catalyze chemical transformations so effectively, there is increasing emphasis on the use of enzyme reactions in commercial processes, and their relatively high cost demands reuse. Typically, if the reaction is performed under homogeneous conditions recovery of the enzyme is difficult and expensive, which effectively precludes homogeneous enzymatic catalysis. The solution to this problem is to insolubilize the enzyme under conditions where a substantial portion of the enzymatic activity exhibited in solution remains under heterogenous reaction conditions.

One particular solution to the aforementioned problem is the construction of immobilized enzyme systems. An immobilized enzyme system consists of a support matrix to which there is bound an enzyme. A support matrix is a structure characterized as having good physical integrity and favorable properties toward liquid flow under conditions experienced in fixed bed reactors, and further characterized by having the ability to bind or immobilize enzymes with minimum perturbation of enzymatic action. By an immobilized enzyme system is meant the structure which results from immobilization of an enzyme on a support matrix.

The binding or immobilization of enzymes to a support matrix is represented by the extremes of physical and chemical binding forces. It is to be recognized that in most cases enzyme immobilization arises from a combination of such binding forces, although often one such force predominates, with the nature of enzyme immobilization generally being determined by the nature of the support matrix. As an example, when the support matrix is a resin, such as one of the phenol-formaldehyde type, binding is predominantly through physical forces. A similar result is obtained when the support matrix is of an ion exchange type. Where the support matrix is comprised of refractory inorganic material, such as inorganic oxides, glass, and ceramics, bearing or impregnated with organic material, for example, polyamines, either bearing pendant functional groups themselves or cross-linked with a bifunctional reagent which provides pendant functional groups, enzyme immobilization arises mainly by chemical reaction of a site on the enzyme with the pendant functional group so as to form a covalent bond. In such an instance binding is, at least predominantly, by chemical means.

An advantage of immobilized enzyme systems where the enzyme is chemically bound to the support matrix is an increased resistance to enzyme loss, as manifested by an increased half-life. In immobilized enzyme systems of the polyamine type cross-linked by excess gluteraldehyde so as to furnish pendant aldehyde groups, as described in U.S. Pat. No. 4,141,857, binding occurs by reaction of the aldehyde group with an amino group from the enzyme. The resultant imine bond, —CH=N—, is susceptible to hydrolysis, which presents a limitation upon the half-life of such covalently bound enzymes.

An object of this invention is to supply an immobilized enzyme system where the enzyme is covalently bound to the support matrix by a hydrolytically stable linkage. An embodiment is a support matrix comprising a porous support impregnated with a polyamine substantially all of whose nitrogens bear a pendant epoxide group. In a more specific embodiment the polyamine is polyethyleneimine. In a still more specific embodiment the pendant epoxide groups are 2,3-epoxypropyl groups.

DESCRIPTION OF THE INVENTION

In one aspect the invention described herein is a support matrix comprising a porous support selected from the group consisting of alumina, silica, thoria, magnesia, porous glass, ceramics, and combinations thereof, impregnated with a polyamine, substantially all of whose nitrogens bear a pendant epoxide group. Another aspect of this invention is a method of preparing the support matrix described above. Still another aspect of this invention is the immobilized enzyme system resulting from covalent bonding of an enzyme to the described support matrix.

The support matrix of this invention is differentiable over the prior art in several major respects. One feature of the present support matrix is its immobilization of enzymes by covalent bonding. This feature alone distinguishes the invention described herein from most of the prior art. But even as to prior art where the support matrix binds convalently to the enzyme, as for example in U.S. Pat. No. 4,141,857, there are important differences. The convalent bond resulting from the instant invention is hydrolytically stable, being a carbon-nitrogen single bond. This is an important feature because enzyme reactions are conducted in aqueous media. Secondly, the epihalohydrins which are used to furnish pendant epoxide groups are a bifunctional reagent heretofore undisclosed in the art pertinent to support matrices. Still another distinguishing feature is that the use of excess epihalohydrin ensures that virtually all nitrogens of the polyamine will bear a pendant epoxide group while ensuring that little cross-linking of polyamine will occur.

The porous supports which may be used in the practice of this invention include materials such as alumina, silica, thoria, magnesia, porous glass, ceramics, and combinations of the above. Factors related to cost and convenience make alumina and especially gamma alumina, a preferred material.

The porous support is then impregnated with a polyamine. One class of polyamines includes the poly(ethyleneamines). These materials are exemplified by diethylenetriamine, triethylenetetraamine, tetraethylenepentamine, pentamethylenehexamine, and polyethyleneimine, with the latter being one of the polyamines of choice.

Another class of polyamines which may be used in this invention are epiamines. An epiamine is the reaction product of an epihalohydrin homopolymer, or a copolymer of epihalohydrin and epoxyalkane monomers, of molecular weight between about 1,000 and 100,000 with an amine. Among the suitable amines are alkylenediamines containing from 2 to about 10 carbon atoms, although alkylene groups containing 2 or 3 carbon atoms are preferred. Linear alkylene groups are more commonly employed than are branched alkylene groups, but the latter may be used, although not necessarily with equivalent results in all cases. Examples of linear alkylene groups include ethylene, propylene, butylene, amylene, hexylene, heptylene, octylene, nonylene, and decylene. Examples of branched alkylene groups include isopropylene, secbutylene, isobutylene, sec-amylene, isoamylene, and so forth. Ethylenediamine, 1,2- and 1,3-diaminopropane are diamines of choice. Amines such as the lower molecular weight poly(ethyleneamine) also may be successfully used in this branch of the invention, and include materials such as diethylenetriamine, triethylenetetramine, tetraethylenepentamine, and pentaethylenehexamine.

The epiamines of this invention are the reaction product of about 1 molar proportion of diamine or polyamine per one equivalent poly(epichlorohydrin). An equivalent of poly(epichlorohydrin) is defined as an amount containing one gram atomic weight of chlorine.

Polyamines generally are used in aqueous solutions containing from about 0.5 to about 10 percent by weight of polyamine, although the concentration is not in any way critical. Generally the porous support and solution of polyamine are contacted with mixing for a time sufficient to ensure impregnation, which is between about 0.5 to about 3 hours. Excess polyamine is then removed, as by decantation of filtration. The polyamine-impregnated porous support is then advantageously dried prior to further treatment, although drying is not absolutely necessary.

The polyamine impregnated support then is contacted with an excess of an epihalohydrin. The purpose of this step is to react all the nitrogens of the impregnated polyamine with the epoxide ring of the halohydrin. For the purpose of this invention an epihalohydrin is an epoxide bearing a halogen on a carbon atom adjacent to one of the carbon atoms bearing the epoxide group. Chlorine, bromine, and iodine may be used, with chlorine being the most desired halogen. The size of the epihalohydrin, as defined by the number of carbon atoms, is not critical, but those containing 3 to 6 carbon atoms are preferred. Among the epihalohydrins which may be employed in this invention are 3-halo-1,2-epoxypropane, 1-halo-2,3-epoxybutane, 3-halo-1,2-epoxybutane, 1-halo-2,3-epoxypentane, 4-halo-2,3-epoxypentane, and so forth. The epihalohydrin of choice is epichlorohydrin.

It is to be emphasized that because an excess of epihalohydrin is used little cross-linking occurs under reaction conditions. By excess is meant an amount of epihalohydrin which is greater than about 2 moles per mole amino groups of the polyamine. Generally at least 5 moles epihalohydrin per mole amino group is used and no theoretical upper limit exists, although practical considerations suggest a cut-off at a mole ratio of about 50.

Reaction of the epihalohydrin with the polyamine occurs at the epoxide group to afford a carbon-nitrogen single bond, an hydroxyl group alpha to the carbon of said bond, and a beta halogen. The partial structure of the organic portion of the support matrix at this point is, using epichlorohydrin as an example,

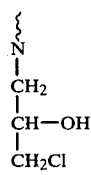

After removal of excess epihalohydrin, treatment with base converts the chlorohydrin structure to an epoxide. The base used for epoxide formation generally is an alkali metal hydroxide, but any reasonably strong base will suffice. Aqueous or alcoholic solutions are most usually employed containing from about 0.5 to about 10 percent by weight of strong base. Treatment with the base is at a temperature most usually between about 40 and about 120° C. for a time from about 2 to about 8 hours. After reaction is complete the support matrix is thoroughly washed with water to remove adsorbed base, and washing is continued until the water washings are neutral. The resulting support matrix is then dried, usually in air, and is in a state for binding of enzymes.

The support matrix so prepared is characterized by having substantially all of the nitrogens of the polyamine bear a pendant epoxide group. In the case where a 3-halo-1,2-epoxypropane is the epihalohydrin, e.g., epichlorohydrin, the partial structure of the pendant group, including the amino nitrogen, is

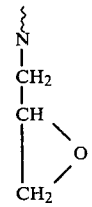

Immobilized enzyme systems may be prepared from the support matrix described above merely by contacting a solution of the enzyme with a support matrix at an appropriate pH. It is to be recognized that the pH used will depend upon the tolerance of the enzyme to various conditions of acidity or alkalinity, and is not related to the ease of reaction of an enzyme amino group with an epoxide from the support matrix. Contacting generally occurs at or below room temperature, although with some stable enzymes immobilization of temperatures up to about 70° C. may be performed. Among the enzymes which may be immobilized in this way, which list is to be considered as illustrative rather than exhaustive, are included glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, lactase, peroxidase, lysozyme, gamma amylase, papain, rennin, ribonuclease and urease.

The examples given below merely illustrate this invention and are not intended to limit it in any way.

EXAMPLE 1

A polyamine-impregnated gamma alumina was prepared by mixing 6 ml of a 2 percent aqueous solution of epiamine per gram of support for 1 hour. The epiamine was prepared by heating ethylenediamine to 100–110° C. and adding to it slowly with stirring an epichlorohydrin homopolymer, of about 2500 average molecular weight, at a ratio of 1 mole equivalent chloromethyl group per 6 moles of ethylenediamine. Heating and stirring were continued for 3 hours. The reaction mixture was then cooled and the HCl formed was neutralized with a 20% aqueous NaOH solution. The precipitated NaCl was removed by filtration and the excess ethylenediamine was removed by vacuum distillation. The resulting viscous product was diluted with water just prior to impregnation of the catalyst support.

Excess aqueous solution was removed by filtration and the solid was air dried. The epiamine-impregnated alumina was then contacted with thorough mixing with a solution of 1 percent of epichlorohydrin in hexane for 5 hours. Excess solution was removed by decantation, and the resulting material was treated with a 2 percent methanolic solution of potassium hydroxide at 22° C. for 1 hour. Solid was recovered by filtration and washed exhaustively with water until the filtrate was neutral.

A solution of glucose isomerase containing 328 units of enzyme per ml of solution was contacted with the support matrix prepared above, in an amount of 12 ml solution per gram support matrix, at 4° C. for about 16 hours. Residual enzyme solution was removed by decantation and the immobilized enzyme system was washed well with deionized water, then loaded into a reactor.

A feedstock of 45 percent by weight Cerelose containing 1,000 ppm $Na_2SO_3$, 5 millimoles per liter $MgSO_4$, 7 ppm sodium omadine at a pH 8.0–8.1 was used at 60° C. and the reactor was operated at a liquid hourly space velocity to ensure $42\pm1$ percent conversion to fructose. An immobilized glucose isomerase system so prepared had an initial activity of 1026 units per gram with a half-life of about 62 days. By comparison a column bearing the same epiamine cross-linked with glutaraldehyde and bearing pendant glutaraldehyde moieties showed an initial activity of 994 units per gram with a half-life of 50 days. Although the difference in initial activity is within experimental error, the increase of 20% in half-life shown by the immobilized glucose isomerase of this invention is quite substantial.

EXAMPLE 2

In this example, the polyamine used was polyethyleneimine, but otherwise the procedure and materials were the same as those described in Example 1. The half-life of the support matrix of this invention was 65 days, whereas that of the polyethyleneimine-glutaraldehyde control was 66 days. Thus this example shows that for polyethyleneimine performance data are comparable for both types of immobilized enzyme systems.

What is claimed is:

1. A support matrix comprising a porous support selected from the group consisting of alumina, silica, thoria, magnesia, porous glass, ceramics, and combinations thereof, impregnated with a polyamine selected from the group consisting of poly(ethyleneamines) and epiamines, substantially all of whose nitrogens bear a pendant epoxide group, wherein said epiamines are the reaction products of polyepichlorohydrin with an alkylenediamine containing from 2 to about 10 carbon atoms.

2. The support matrix of claim 1 where the support is alumina.

3. The support matrix of claim 1 where the polyamine is selected from the group consisting of diethylenetriamine, triethylenetetramine, tetraethylenepentamine, pentamethylenehexamine, and polyethyleneimine.

4. The support matrix of claim 3 where the polyamine is polyethyleneimine.

5. The support matrix of claim 1 where the alkylenediamine is selected from the group consisting of ethylenediamine, 1,2-diaminopropane, and 1,3-diaminopropane.

6. The support matrix of claim 1 where the group pendant to the nitrogen of the polyamine is a 2,3-epoxypropyl group.

7. A method of making a support matrix comprising impregnating a porous support selected from the group consisting of alumina, silica, thoria, magnesia, porous glass, ceramics, and combinations thereof with a polyamine selected from the group consisting of poly(ethyleneamines) and epiamines wherein said epiamines are the reaction products of polyepichlorohydrin with an alkylenediamine containing from 2 to about 10 carbon atoms, removing excess polyamine, treating the impregnated support with an excess of an epihalohydrin so as to react substantially all of the nitrogens of the polyamine with the epihalohydrin, removing excess unreacted epihalohydrin, contacting the resulting material with base so as to regenerate an epoxide moiety, removing excess base, and recovering the resulting support matrix.

8. The method of claim 7 where the support is alumina.

9. The method of claim 7 where the polyamine is selected from the group consisting of diethylenetriamine, triethylenetetramine, tetraethylenepentamine, pentamethylenehexamine, and polyethyleneimine.

10. The method of claim 9 where the polyamine is polyethyleneimine.

11. The method of claim 7 where the epihalohydrin contains from about 3 to about 6 carbon atoms.

12. The method of claim 11 where the epihalohydrin is a 3-halo-1,2-epoxypropane.

13. The method of claim 12 where the epihalohydrin is 3-chloro-1,2-epoxypropane.

14. An immobilized enzyme system comprising the support matrix of claim 1 having an enzyme covalently bonded thereto.

15. The immobilized enzyme system of claim 14 where the enzyme is selected from the group consisting of glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, lactase, peroxidase, lysozyme, gamma amylase, papain, rennin, ribonuclease and urease.

* * * * *